United States Patent
Shalaby

(10) Patent No.: US 8,952,075 B2
(45) Date of Patent: *Feb. 10, 2015

(54) BIOACTIVE POLYMERIC LIQUID FORMULATIONS OF ABSORBABLE, SEGMENTED ALIPHATIC POLYURETHANE COMPOSITIONS

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/454,774

(22) Filed: May 22, 2009

(65) Prior Publication Data

US 2009/0291925 A1 Nov. 26, 2009

Related U.S. Application Data

(60) Provisional application No. 61/128,487, filed on May 22, 2008.

(51) Int. Cl.
| | |
|---|---|
| A61K 47/34 | (2006.01) |
| A61K 47/30 | (2006.01) |
| A61K 31/335 | (2006.01) |
| A61K 31/07 | (2006.01) |
| A61K 47/10 | (2006.01) |
| A61K 31/337 | (2006.01) |
| A61K 31/397 | (2006.01) |
| A61K 31/407 | (2006.01) |
| A61K 31/4174 | (2006.01) |
| A61K 31/42 | (2006.01) |
| A61K 31/496 | (2006.01) |
| A61K 31/513 | (2006.01) |
| A61K 31/555 | (2006.01) |
| A61K 31/65 | (2006.01) |
| A61K 9/00 | (2006.01) |

(52) U.S. Cl.
CPC ............... *A61K 47/10* (2013.01); *A61K 31/337* (2013.01); *A61K 31/397* (2013.01); *A61K 31/407* (2013.01); *A61K 31/4174* (2013.01); *A61K 31/42* (2013.01); *A61K 31/496* (2013.01); *A61K 31/513* (2013.01); *A61K 31/555* (2013.01); *A61K 31/65* (2013.01); *A61K 47/34* (2013.01); *A61K 9/0014* (2013.01); *A61K 9/0019* (2013.01)
USPC ....................... 514/772.3; 514/772.7; 514/452; 514/724

(58) Field of Classification Search
USPC ................... 514/452, 724, 772.1, 772.7, 668
See application file for complete search history.

(56) References Cited

U.S. PATENT DOCUMENTS

| | | | |
|---|---|---|---|
| 5,653,992 A | 8/1997 | Bezwada | |
| 5,714,159 A | 2/1998 | Shalaby | |
| 6,413,539 B1 | 7/2002 | Shalaby | |
| 6,872,797 B2 * | 3/2005 | Ueno et al. | 528/85 |
| 7,795,467 B1 * | 9/2010 | Pacetti et al. | 560/336 |
| 7,858,078 B2 * | 12/2010 | Hadba et al. | 424/78.27 |
| 2006/0286143 A1 * | 12/2006 | Shalaby et al. | 424/423 |
| 2009/0233887 A1 * | 9/2009 | Shalaby et al. | 514/154 |
| 2012/0208789 A1 * | 8/2012 | Shalaby et al. | 514/152 |

OTHER PUBLICATIONS

U.S. Appl. No. 12/380,381, filed Feb. 26, 2009, Shalaby.

* cited by examiner

*Primary Examiner* — Renee Claytor
*Assistant Examiner* — Shobha Kantamneni
(74) *Attorney, Agent, or Firm* — Douglas L. Lineberry

(57) ABSTRACT

Bioactive liquid formulations are formed of combinations of absorbable, segmented aliphatic polyurethane compositions and liquid polyether for use as vehicles for the controlled release of at least one active agent for the conventional and unconventional treatment of different forms of cancer and the management of at least one type of bacterial, fungal, and viral infection.

1 Claim, No Drawings

BIOACTIVE POLYMERIC LIQUID FORMULATIONS OF ABSORBABLE, SEGMENTED ALIPHATIC POLYURETHANE COMPOSITIONS

The present application claims the benefit of prior provisional U.S. Ser. No. 61/128,487, filed May 22, 2008.

FIELD OF THE INVENTION

This invention is directed to bioactive polymeric liquid formulations of absorbable, segmented aliphatic polyurethane compositions which are formed of macromolecular polyether-carbonate-urethane, polyether-carbonate-urethane-urea, and polyether-ester-urethane chains in combination with liquid polyethers for use as controlled release vehicles for at least one drug capable of exhibiting at least one function associated with antibacterial, antifungal, antiviral, and/or antineoplastic activity.

BACKGROUND OF THE INVENTION

Advanced developments in the area of absorbable polymers and particularly those dealing with liquids and hydrogel-forming liquids made of copolyester and polyether-esters, respectively, were paralleled by a similarly advanced development of controlled drug delivery systems by the present inventor and coworkers for use as extrudable or injectable liquid formulations for use in parenteral and topical applications (U.S. Pat. Nos. 5,653,992; 5,714,159; 6,413,539). Pertinent to the present invention are the injectable hydrogel-forming, self-solvating, liquid, absorbable, segmented polyether-esters, which are used, in part, for the controlled release of antibacterial agents, such as doxycycline, for the treatment of periodontitis (U.S. Pat. Nos. 5,714,159; 6,413,539). The main attributes of hydrogel-forming liquid polyether-esters include their ease of application topically and as an injectable formulation without the need of using an organic solvent. However, until a recent disclosure by the present inventor (U.S. Patent Application Ser. No. 61/069,046), and in spite of the extensive development and use of segmented polyurethanes for biomedical application, the prior art was silent on the development of absorbable, segmented polyurethane compositions, which can be used independently or as part of a polymeric liquid formulation for the controlled release of a broad range of bioactive agents for use in topical, parenteral, and/or injectable applications. In effect, the only cited disclosure that is most pertinent to the instant invention is that of Shalaby et al. (U.S. Patent Application Ser. No. 61/069,046), which dealt, in part, with hydroswellable, absorbable, aliphatic segmented polyurethanes and polyurethane-ureas capable of swelling in the biological environment. Attributes associated with these polymers and the technological and clinical success of the hydrogel-forming liquid polyether-esters discussed above, provided the incentive to pursue the study associated with the present invention.

SUMMARY OF THE INVENTION

The present invention is directed to a bioactive polymeric liquid formulation comprising a blend of an absorbable, segmented, aliphatic polyurethane, a liquid polyoxyalkylene and at least one drug selected from doxycycline, mitomycin, clindamycin, miconazole, clotrimazole, ketoconazole, fluconazole, butoconazole, tioconazole, leflunomide, 5-fluorouracil, paclitaxel, carboplatin, mycophenolic acid, podophyllinic acid, podophyllotoxin and related bioactive compounds, wherein the liquid polyoxyalkylene comprises chains of at least one type of oxyalkylene sequence selected from oxyethylene, oxypropylene, and oxytrimethylene. The polyurethane composition comprises polyoxyalkylene chains covalently linked to alkylene carbonate chains, wherein the polyalkylene carbonate chains are interlinked with aliphatic urethane segments, wherein the alkylene carbonate chains comprise trimethylene carbonate sequences and the aliphatic urethane segments are derived from at least one diisocyanate selected from the group consisting of tetramethylene diisocyanate, hexamethylene diisocyanate, lysine-derived diisocyanate, and cyclohexane bis(methylene isocyanate), and wherein the segmented polyurethane is made by the method comprising the steps of end-grafting polyethylene glycol having a molecular weight of about 400 Da with trimethylene carbonate, and interlinking the end-grafted polyethylene glycol with hexamethylene diisocyanate. And such formulation is used as (a) a vehicle for the controlled release of at least one antineoplastic agent for treating at least one type of cancer selected from breast, ovarian, cervical, lung, prostate, testicular, and skin cancer, wherein said formulation contains at least one antineoplastic agent is selected from the group consisting of paclitaxel, 5-fluorouracil, podophyllinic acid, mycophenolic acid, and carboplatin, alternatively, the said vehicle contains at least one antineoplastic agent is selected from antimicrobial agents and immunosuppressant agents selected from the group consisting of doxycycline, tetracycline, mitomycin, clindamycin, miconazole, ketoconazole, fluconazole, and leflunomide; (b) a vehicle for the controlled release of at least one antifungal agent for treating vaginal yeast, nail and skin fungal infections, the agent selected from the group consisting of miconazole, ketoconazole, butoconazole, clotrimazole; (c) a vehicle for the controlled release of at least one antibacterial agent for treating vaginal and skin bacterial infections, the agent selected from the group consisting of doxycycline, mitomycin, and clindamycin; (d) a vehicle for the controlled release of at least one antibacterial agent for treating periodontitis and related dental infections, the agent selected from the group consisting of doxycycline, tetracycline, clindamycin, and mitomycin; and (e) a vehicle for the controlled release of at least one agent for treating genital, nail, and skin warts, and related infections, the agent selected from the group consisting of paclitaxel, 5-fluorourecil, podophyllinic acid, podophyllotoxin, miconazole, ketoconazole, butoconazole, fluconazole, and clotrimazole.

A key aspect of this invention deals with a bioactive polymeric liquid formulation which is a blend of an absorbable, segmented, aliphatic polyurethane, a liquid polyoxyalkylene and at least one drug selected from doxycycline, mitomycin, clindamycin, miconazole, clotrimazole, ketoconazole, fluconazole, butoconazole, tioconazole, leflunomide, 5-fluorouracil, paclitaxel, carboplatin, mycophenolic acid, podophyllinic acid, podophyllotoxin and related bioactive compounds, wherein the polyurethane composition comprises an aliphatic polyurethane-urea comprising polyoxyalkylene chains covalently linked to polyalkylene-urethane chains wherein the polyalkylene-urethane chains are further interlinked with aliphatic urea chain segments, and wherein the polyoxyalkylene chains comprise at least one type of oxyalkylene sequence selected from the group consisting of oxyethylene, oxypropylene, and oxytrimethylene and the urethane chain segments are derived from at least one diisocyanate selected from the group consisting of hexamethylene diisocyanate, lysine-derived diisocyanate, and cyclohexane bis (methylene isocyanate), and wherein the resulting polyoxyalkylene urethane molecules having at least one isocyanate terminal group are chain extended with an alkylene diamine selected from the group consisting of ethylene-, trimethylene-, and hexamethylene-diamine, thereby forming polyurethane-urea segmented chains. And such formulation is used as a vehicle for the controlled release of at least one antineoplastic agent for treating at least one type of cancer selected from breast, ovarian, cervical, lung, prostate, testicular, and skin cancer, wherein the at least one antineoplastic agent is selected from the group consisting of paclitaxel, 5-fluorouracil, podophyllinic acid, mycophenolic acid, and carboplatin. Alternatively, the vehicle contains at least one antineoplastic agent is selected from antimicrobial agents and immunosuppressant agents selected from the group consisting of doxycycline, tetracycline, mitomycin, clindamycin, miconazole, ketoconazole, fluconazole, and leflunomide.

Another key aspect of this invention deals with a bioactive polymeric liquid formulation which is a blend of an absorbable, segmented, aliphatic polyurethane, a liquid polyoxyalkylene and at least one drug selected from doxycycline, mitomycin, clindamycin, miconazole, clotrimazole, ketoconazole, fluconazole, butoconazole, tioconazole, leflunomide, 5-fluorouracil, paclitaxel, carboplatin, mycophenolic acid, podophyllinic acid, podophyllotoxin and related bioactive compounds, wherein the polyurethane composition comprises a polyether-ester-urethane comprising polyoxyalkylene chains covalently linked to polyester chain segments, wherein the polyester chains are interlinked with aliphatic urethane segments, wherein the polyester chain segments comprise polyester-carbonate chain segments, and further wherein the polyester chain segments are derived from at least one cyclic monomer selected from the group consisting of ε-caprolactone, p-dioxanone, 1,5-dioxepan-2-one, trimethylene carbonate, 1-lactide, glycolide, dl-lactide, and a morpholinedione. Such formulation is used (a) as a vehicle for the controlled release of at least one antineoplastic agent for treating at least one type of cancer selected from breast, ovarian, cervical, lung, prostate, testicular, and skin cancer, wherein the at least one antineoplastic agent is selected from the group consisting of antineoplastic agents consisting of paclitaxel, 5-fluorouracil, podophyllinic acid, mycophenolic acid, and carboplatin, and alternatively, the said vehicle contains at least one antineoplastic agent is selected from antimicrobial agents and immunosuppressant agents selected from the group consisting of doxycycline, tetracycline, mitomycin, clindamycin, miconazole, ketoconazole, fluconazole, and leflunomide; (b) as a vehicle for the controlled release of at least one antibacterial agent for treating periodontitis and related dental infections, the agent selected from the group consisting of doxycycline, tetracycline, clindamycin, and mitomycin; and (c) as a vehicle for the controlled release of at least one agent for treating fungus-infected nails and genital and skin warts, and related infections, the agent selected from the group consisting of paclitaxel, 5-fluorourecil, podophyllinic acid, podophyllotoxin, miconazole, ketoconazole, butoconazole, fluconazole, and clotrimazole.

DETAILED DESCRIPTION OF PREFERRED EMBODIMENTS

The present invention is directed to bioactive, polymeric, liquid formulations which are absorbable, segmented, aliphatic liquid polyurethane compositions or a combination thereof with a liquid polyether. The absorbable, segmented, aliphatic polyurethane compositions comprise polyether-carbonate-urethane-urea, polyether-carbonate-urethanes, polyether-carbonate-ester-urethane, and/or polyether-ester-urethane. These polyurethane compositions, and preferably the combination with a liquid polyether to reduce their viscosities, are selected to be easily applied topically as drug-loaded formulations, which can be also extruded or injected by syringe or collapsible dispenser into the biological site. Some of these formulations, particularly those containing a water-soluble liquid polyethylene glycol, tend to undergo gelation or at least swelling upon contacting the liquid environment at the application site. The extent of swelling or gelation is used to control the drug release profile by adjusting the hydrophilicity of the polyurethane compositions and/or the fraction of the polyethylene glycol. This strategy is used to control the diffusion of the active agent and hence its release profile. As to the types of bioactive agents, subject of this invention, in terms of their intended use in a traditional and well-established manner, they fall into five main categories, namely: (1) antibacterial as in doxycycline, mitomycin, clindamycin; (2) antifungal as in miconazole, clotrimazole, tioconazole, and ketoconazole; (3) antineoplastic as in 4-fluorouracil, paclitaxel, carboplatin, mycophenolic acid, and podophyllinic acid; (4) antiviral as in podophyllotoxin; and (5) immunosuppressive as in leflunomide. A unique aspect of the bioactive agents, subject of this invention, is the newly coined category of drugs which are denoted in the instant application as crossover bioactive agents, each of which has a primary function and yet exhibits at least one additional function that is distinctly different from its primary function. Given in Table I are typical examples that are part of this invention and were not cited in the prior art or can be considered obvious to those familiar with the biochemical, physiological, and pharmacological aspects of drugs.

TABLE I

| Typical Crossover Bioactive Agents | | |
|---|---|---|
| Drug Name | Primary Clinical Use | Additional Uses and Properties |
| Miconazole | Antifungal | Antineoplastic (as per testing with ovarian cancer cell lines (SKOV3 and OVCAR). |
| Fluconazole | Antifungal | Antineoplastic (as per testing with ovarian cancer cell lines (SKOV3 and OVCAR). |
| Mitomycin | Antibacterial | Antineoplastic, as per testing with ovarian cell lines (SKOV3 and OVCAR). |
| Clindamycin | Antibacterial | Antineoplastic, as per testing with ovarian cell lines (SKOV3 and OVCAR). |
| Paclitaxel | Antineoplastic | Antibacterial as per testing with *S aureous* |
| 5-Fluorouracil | Antineoplastic | Antibacterial as per testing with *S aureous* |
| Leflunomide | Immunosuppressant | Antineoplastic, as per testing with ovarian cell lines (SKOV3 and OVCAR). |

From a clinical perspective, this invention provides bioactive formulations that are useful for treating bacterial, fungal, and viral infections as well as different forms of cancers. A key aspect of this invention deals with the crossover drugs having multipurpose functions as in the case of (1) miconazole and fluconazole, which are not only useful for treating yeast infections, but also exhibit antineoplastic and antiviral activities and thereby are applicable for treating several forms of cancer and treatment of human immunodeficiency virus (HIV); (2) leflunomide, which is not only an immunosuppressant, but also useful as an antineoplastic agent for treating different forms of cancer as well as an antiviral agent for managing HIV infection; and (3) mitomycin and clindamycin, which are not only antibacterial agents, but also exhibit antineoplastic and antiviral activities and thereby are useful for treating different forms of cancer and managing HIV infection, respectively; and (4) paclitaxel and 5-fluorouracil, which are not only antineoplastic agents, but are also useful for treating bacterial infections and managing HIV infection.

For the preparation of certain bioactive formulations, there may be (1) no need to use the liquid polyether as in the case of the polyurethane composition, which is sufficiently flowable and its viscosity allows the final formulation to be injectable through a syringe or extrudable through a squeezable dispenser; (2) a need to use microparticular anion-exchangers made of carboxyl-terminated polyglycolide similar to that described in U.S. Pat. Nos. 5,714,159 and 6,413,539 should the active agent be basic and can interact ionically with the anion-exchanger thereby modulating its release profile; and (3) a need to prepare a low viscosity diluent polyurethane composition having a high polyether content, but having qualitatively the same component as the polyurethane composition used as the main vehicle.

Further illustrations of the present invention are provided by the following examples:

EXAMPLE 1

Synthesis and Characterization of a Typical Polyether-carbonate-urethane, P1

This was conducted following the teaching of U.S. Patent Application Ser. No. 61/069,046 as described below:

For an initial charge, poly(ethylene glycol) ($M_n$=400 Da) (0.15 moles) and tin(II) 2-ethyl hexanoate (3.53×10$^4$ moles) was added to a 500 mL, 3-neck, round-bottom flask equipped with a PTFE coated magnetic stir bar. The contents were heated to 70° C. and allowed to stir for 10 minutes. For a second charge, trimethylene carbonate (0.882 moles) was added and the contents were heated to 135° C. Conditions were maintained until practically complete monomer conversion was achieved. The magnetic stir bar was removed and replaced by a stainless steel mechanical stirrer. The polymer was cooled to room temperature. For a third charge, 1,6-diisocyanatohexane (0.12 moles) was added and the contents were stirred until complete mixing was achieved. The contents were stirred and heated to 100° C. Conditions were maintained for 1.25 hours. The polymer was allowed to cool to room temperature and then dissolved in an equal part of tetrahydrofuran. The polymer solution was treated with 5 mL of 2-propanol at 55° C. then precipitated in cold water. The purified polymer was isolated and dried to a constant weight at 55° C. on a rotary evaporator. The purified polymer was characterized for molecular weight by GPC using tetrahydrofuran as the mobile phase which resulted in an $M_n$, $M_w$, $M_p$, and PDI of 11 kDa, 19 kDa, 18 kDa, and 1.7 respectively. Identity and composition were confirmed by FT-IR and NMR, respectively.

EXAMPLE 2

Preparation and Evaluation of Doxycycline-Containing Formulation F1-A Using the Polyurethane Composition P1 of Example 1

The polyurethane composition of Example 1 (4.0 g) was heated to 50° C. and mixed thoroughly with polyethylene glycol having a molecular weight of 400 Da (6.0 g). To this (without additional heating) was added a mixture of doxycycline hydrochloride (1.5 g) and microparticles of carboxyl-terminated polyglycolide (0.75 g) having an average diameter of <10 micron (prepared as described in U.S. Pat. Nos. 5,714, 159 and 6,413,539). All components were mechanically mixed at room temperature until a uniform dispersion is obtained (as determined microscopically). The flow property of the formulation is measured in terms of complex viscosity using a parallel plate rheometer.

To determine the release profile of doxycycline, aliquots of the formulation F1-A were incubated in a buffered solution at 37° C. and 7.2 pH for predetermined periods of time. At the conclusion of each period, the buffer solution is decanted and replaced by a fresh aliquot. The decanted buffer was analyzed by HPLC to determine the amount of doxycycline released. Over a period of 600 hours, about 25, 30, 35, 45, and 55 percent of the days was released at 50, 100, 200, 300, and 600 hours respectively, was released.

EXAMPLE 3

Preparation and Evaluation of Doxycycline-Containing Formulation F1-B Using the Polyurethane/Composition of P1 of Example 1

This was conducted as described in Example 2 with the exception of using different amounts of P1 (5 g) and PEG-400 (5 g). Results of the drug release indicated about 22, 32, 38, 43, and 57 percent of the drug released at 50, 100, 200, 300, and 600 hours, respectively.

EXAMPLE 4

Synthesis and Characterization of Polyether-ester-urethane: General Method

This was conducted following the teaching of U.S. Patent Application Ser. No. 61/069,046 as described below:

For an initial charge, poly(ethylene glycol) ($M_n$=400 Da) and tin(II) 2-ethyl hexanoate was added to a 500 mL, 3-neck, round-bottom flask equipped with a PTFE coated magnetic stir bar. The contents were heated to 70° C. and allowed to stir for 10 minutes. For a second charge, dl-lactide and glycolide were added and the contents were heated to 135° C. Conditions were maintained until practically complete monomer conversion was achieved. The magnetic stir bar was removed and replaced with a stainless steel mechanical stirrer. The polymer was cooled to room temperature. For a third charge, 1,6-diisocyanatohexane was added and the contents were stirred until complete mixing was achieved. The contents were stirred and heated to 100° C. Conditions were maintained for 1.25 hours. The polymer was allowed to cool to room temperature and then dissolved in an equal part of tetrahydrofuran. The polymer solution was treated with 5 mL of 2-propanol at 55° C. then precipitated in cold water. The purified polymer was dried to a constant weight at 55° C. on a rotary evaporator. The purified polymer was characterized for molecular weight by GPC using tetrahydrofuran as the mobile phase. Identity and composition were confirmed by FT-IR and NMR, respectively.

EXAMPLE 5

Synthesis and Characterization of Typical Polyether-ester-urethanes Using the General Method of Example 2, P2, P3, and P4

This was conducted following the teaching of U.S. Patent Application Ser. No. 61/069,046 as described below:

Polyether-ester-urethanes P-2, P-3, and P-4 were prepared using the method of Example 4 with 0.10, 0.225, 0.15 moles of poly(ethylene glycol) ($M_n$=400 Da), $1.73 \times 10^{-4}$, $3.18 \times 10^{-4}$, $2.60 \times 10^{-4}$ moles of tin(II) 2-ethyl hexanoate, 0.35, 0.64, 0.52 moles of dl-lactide, 0.09, 0.16, 0.13 moles of glycolide, and 0.12, 0.18, 0.12 moles of 1,6-diisocyanatohexane, respectively. Polymers P-2, P-3, and P-4 were characterized for molecular weight by GPC using tetrahydrofuran as the mobile phase which resulted in $M_n$ of 12, 9, and 9 kDa, $M_w$ of 26, 14, and 15 kDa, $M_p$ of 22, 12, and 14 kDa, and PDI of 2.1, 1.6, and 1.6, respectively. Identity and composition were confirmed by FT-IR and NMR, respectively.

EXAMPLE 6

Preparation and Evaluation of Bioactive Formulations Using Polyurethane Composition P2 from Example 5: General Method An aliquot of P2 (4.5 g) was heated to 50° C. then mixed thoroughly at that temperature with polyethylene glycol (PEG-400) having a molecular weight of 400 Da (4.4 g). The mixed polymers were allowed to reach room temperature and then thoroughly mixed with a second aliquot of PEG-400 (1.1 g) premixed with the drug solution in ethanol. The final formulation was dried under reduced pressure to distill the ethanol prior to conducting the drug release study. The release profile of the specific drug in the respective formulation was conducted using buffered solution and HPLC as described in Example 4, with the exception of using a buffered saline solution at pH 7.4.

EXAMPLE 7

Preparation and Evaluation of Leflunomide-Containing Formulation F2-A

Following the general method of Example 6, an aliquot of an ethanol stock solution (100 mg/mL) was used to provide a drug concentration in the final formulation of 1.83 weight percent. The drug release results indicated a 0.5, 0.9, and 1.0 percent release at day 1, 3, and 10, respectively.

EXAMPLE 8

Preparation and Evaluation of Paclitaxel-Containing Formulation F2-B

Following the general method of Example 6, an aliquot of an ethanol stock solution (3.33 mg/mL) was used to provide a drug concentration in the final formulation of 0.009 weight percent. The drug release results indicated 1.7 and 1.9 percent release at 1 and 7 days, respectively.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A bioactive polymeric liquid formulation comprising:
an absorbable, segmented, aliphatic polyurethane comprising polyoxyalkylene chains end-grafted with alkylene carbonate chains that include trimethylene carbonate sequences, the end-grafted polyoxyalkylene chains interlinked with aliphatic urethane segments that are derived from at least one diisocyanate selected from the group consisting of tetramethylene diisocyanate, hexamethylene diisocyanate, lysine-derived diisocyanate, and cyclohexane bis(methylene isocyanate), forming a polymer with an alternating chain structure of aliphatic urethane-alkylene carbonate-polyoxyalkylene-alkylene carbonate-aliphatic urethane;
wherein the polyoxyalkylene comprises poly(ethylene glycol) having a molecular weight of 400 Da;
at least one drug selected from the group consisting of doxycycline, mitomycin, clindamycin, miconazole, clotrimazole, ketoconazole, fluconazole, butoconazole, tioconazole, leflunomide, 5-fluorouracil, paclitaxel, carboplatin, mycophenolic acid, podophyllinic acid, podophyllotoxin; and
wherein the polyurethane is treated with 2-propanol to eliminate any unreacted isocyanate groups.

* * * * *